United States Patent [19]

Chauvin et al.

[11] Patent Number: 4,533,500
[45] Date of Patent: Aug. 6, 1985

[54] PROCESS FOR MANUFACTURING N-ACYLIMINODIACETIC ACIDS

[75] Inventors: Yves Chauvin, Le Pecq; Dominique Commereuc, Meudon; André Hirschauer, Montesson; Dominique Reffet, Rueil-Malmaison; Robert Stern, Paris, all of France

[73] Assignees: Institut Francais Du Petrole, Rueil-Malmaison; Societe Nationale Elf-Aquitaine (Production), Paris La Defense, both of France

[21] Appl. No.: 476,295

[22] Filed: Mar. 17, 1983

[30] Foreign Application Priority Data

Mar. 17, 1982 [FR] France ................. 82 04669

[51] Int. Cl.$^3$ ............... C09F 5/00; C09F 7/00; C11C 3/00
[52] U.S. Cl. ................. 260/404; 260/404.5; 560/153; 560/171; 562/423; 562/518; 562/571; 556/134

[58] Field of Search ......... 260/404, 404.5 R, 404.5 A; 562/450, 503, 505, 506, 509, 565, 571, 518, 423, 571; 560/171, 153

[56] References Cited

U.S. PATENT DOCUMENTS

| | | |
|---|---|---|
| 3,260,745 | 7/1966 | Andress, Jr. et al. ............... 562/553 |
| 3,766,266 | 10/1973 | Wakamatsu et al. ............ 260/404 X |
| 3,904,668 | 9/1975 | Gaudette et al. ................ 562/571 X |
| 4,264,515 | 4/1981 | Stern et al. ........................ 260/404 |

*Primary Examiner*—Helen M. S. Sneed
*Attorney, Agent, or Firm*—Millen & White

[57] ABSTRACT

N-acyliminodiacetic acids are manufactured by reacting formaldehyde or a formaldehyde generator compound with a N-unsubstituted amide or a generator thereof and with carbon monoxide in contact with a carbonylation catalyst, for example, a cobalt compound, the ratio of the aldehyde groups to the amide groups being at least 2:1. The formaldehyde generator can be a polymeric form of formaldehyde and the amide generator can be a carboxylic ester, acid or anhydride.

8 Claims, No Drawings

PROCESS FOR MANUFACTURING N-ACYLIMINODIACETIC ACIDS

BACKGROUND OF THE INVENTION

This invention relates to a process for manufacturing N-acyliminodiacetic acids.

A known process for manufacturing N-acylaminoacids consists of reacting an aldehyde with an amide in the presence of carbon monoxide and of a carbonylation catalyst (U.S. Pat. No. 3,766,266); the reactants (adehyde and amide) may be formed in situ. It is stated that the use of aldehyde and amide in equimolecular proportions is normally more advantageous although an excess of the cheaper reactant may be used to increase the yield.

SUMMARY OF THE INVENTION

It has now been found, and this is the object of this invention, that N-acyliminodiacetic acids can be obtained with a good yield by reacting formaldehyde or a formaldehyde generator with an amide or an amide generator and with carbon monoxide in a ratio of at least 2:1 of formaldehyde (or formaldehyde generator) to the amide groups (or the generators of these groups) in the presence of a carbonylation catalyst.

This result could not be expected from the teaching of the above patent and offers an obvious interest in view of the uses of the resultant products, as hereinafter disclosed.

The reaction can be represented by the following equation:

$$2H_2CO + RCONH_2 + 2CO \rightarrow RCON(CH_2COOH)_2$$

wherein R is hydrogen or an organic group as defined below.

Useful amines, according to the invention, are mono- or polyamides free of substituent on the nitrogen atom, the radical R being an aliphatic, cycloaliphatic, aromatic or heterocyclic radical or one such radical bearing purely hydrocarbon substituents or one or more functional groups inert to the reaction, for example carboxylic acid groups or ester groups. These amides comprise, without limitation of the invention: formamide, acetamide, propionamide, butyrate, stearylamide, acrylamide, adipamide, sebacamide, compounds of the $R_1CH(CH_2CONH_2)_2$ type or polymers comprising amide groups such as polyacrylamide. $R_1$ is hydrogen or a hydrocarbyl radical having the same definition as R.

The amide generating compounds, in the reaction conditions, are nitriles in the presence of water, ammonium salts of carboxylic acids and carboxylic acids, esters, and anhydrides in the presence of ammonia.

Formaldehyde can be used as such or in aqueous solution, or as a formaldehyde generator, for example as trioxymethylene or polyoxymethylene or as formacetal or formacylate.

The reaction conditions are conventional for the oxo reaction.

The carbonylation catalyst which can be used in the invention are more particularly the transition metals used in the hydroformylation or carboxylation reactions, such as metals of group VIII of the periodic classification and more particularly cobalt. Although the form under which cobalt is present in the reaction is not known with certainty, it is thought that it appears as carbonyl derivatives; all the cobalt compounds able to lead to the formation of carbonyl derivatives in the condition of the reaction may be used, for example, cobalt octoate, cobalt acetate and dicobalt octacarbonyl.

The amount of catalyst to be used depends on the reaction conditions and is advantageously selected between 1:10 and 1:1000 by mole with respect to the reacted amide or its precursor.

The reaction temperature is selected between 30° and 250° C., preferably between 50° and 150° C. The partial carbon monoxide pressure is preferably selected between 5,000 and 30,000 kPa. It may be advantageous to operate in the presence of hydrogen whose partial pressure may range from 0 to 10,000 kPa.

The reaction can be conducted in the presence of any one of the various solvents conventionally used in the hydrofomylation or carbonylation reactions, for example alcohols, ethers, esters, particularly dioxane and ethyl acetate. It is also advantageous to operate in the presence of water in such an amount that the molar ratio of water to formaldehyde be comprised between 0 and 25 and preferably between 0.4 and 10.

According to the invention, the molar ratio of formaldehyde to the amide must be at least 2:1 but the diacid yield can be improved by increasing this ratio, for example up to 3:1. These conditions thus differ from those of the U.S. Pat. No. 3,766,266.

At the end of the reaction, the N-acyliminodiacetic acid may be isolated from the medium by crystallization or by any other method known in the art.

The N-acyliminodiacetic acids and their derivatives can be used as complexing agents for heavy metals, for example as demetallization agents for lye and in bleaching solutions, as anti-corrosion agents, as stabilizers for chlorinated polymers as zinc or calcium salts, as detergents, in the form of alkali metal salts, particularly for stabilizing emulsions. They can be converted to iminodiacetic acid by hydrolysis of the imide group. As detergents, they find use in enhanced oil recovery.

The following examples illustrate the invention without limiting the scope thereof.

EXAMPLE 1

8.85 g (0.15 mole) of acetamide, 13.5 g (0.45 mole) of paraformaldehyde, 8.1 g (0.45 mole) of water, 120 ml of dioxane and 1 g of dicobalt octacarbonyl are introduced into a 300 ml stainless steel reactor equipped with a magnetic stirrer and a heating system. The pressure in the reactor is raised to 13,000 kPa of a gaseous carbon monoxide/hydrogen mixture in a molar ratio of 1:1 and the temperature is then raised to 80° C. After 3 hours, the gas absorption amounts to 0.38 mole.

After cooling, the content of the reactor is analysed; it amounts to 0.296 acid equivalent. The analysis by vapor phase chromatography of the esterification product shows the formation of 0.097 mole of N-acetyliminodiacetic acid.

EXAMPLE 2

28.3 g (0.1 mole) of stearylamide, 9 g (0.3 mole) of paraformaldehyde, 5.4 g (0.3 mole) of water, 120 ml of dioxane and 1 g of dicobaltoctacarbonyl are introduced into the same apparatus as used in example 1. The reactor pressure is raised to 13,000 kPa of the same gas mixture and the temperature is raised to 110° C. A gas absorption of 0.28 mole is observed after 1 h 30.

After cooling, the contents of the reactor are analyzed and 0.172 acid equivalent is found. After evaporation of dioxane and water-washing, a white solid is obtained which is recrystallized in a 70:30 by volume mixture of heptane and ethyl acetate. The resultant product has been analyzed by elemental analysis (Carbon: found 66.03%, calculated 66.16%. Hydrogen: found 10.48%, calculated 10.98%. Nitrogen: found 3.69%, calculated 3.50%. Oxygen: found 19.70%, calculated 20.05%). $C_{22}H_4NO_5$. The analysis has been confirmed by N.M.R. (nuclear magnetic resonance). The product is N-stearyliminodiacetic acid.

Melting point: 89° C.

EXAMPLE 3

20 g (0.1 mole) of a laurylamide, 9 g (0.3 mole) of paraformaldehyde, 5.4 g (0.3 mole) of water, 120 ml of dioxane and 1 g of dicobaltoctacarbonyl are introduced into the same apparatus as used in example 1. The pressure is raised to 13,000 kPa of the same gas mixture and the temperature is raised to 110° C. 0.28 mole of gas are absorbed in 1 h 30.

After cooling and treating as in example 2, the product has been characterized (elemental analysis, mass spectrometry and N.M.R.) as being N-lauryliminodiacetic acid (Carbon: found 61.39%, calculated 60.95%. Hydrogen: found 9.45%, calculated 9.21%. Nitrogen: found 4.62%, calculated 4.44%. Oxygen: found 24.48%, calculated 25.40%. Melting point: 82° C.

EXAMPLE 4

17.2 g (0.15 mole) of hexanoic acid amide, 13.5 g (0.45 mole) of paraformaldehyde, 8.1 g (0.45 mole) of water, 120 ml of dioxane and 1 g of dicobaltoctacarbonyl are introduced into the same apparatus as used in example 1. The pressure is raised to 13,000 kPa of the same gas mixture and the temperature is raised to 110° C. After 2 h, the gas absorption amounts to 0.37 mole.

After cooling, the content of the reactor is analyzed and found to contain 0.268 acid equivalent. The analysis of the esterification product by vapor phase chromatography shows the presence of 0.084 mole of N-hexanoyliminodiacetic acid.

EXAMPLE 5

8.85 g (0.15 mole) of acetamide, 45 g of a 30% aqueous solution of formaldehyde (0.45 mole), 130 ml of dioxane and 1 g of dicobaltoctacarbonyl are introduced into the same apparatus as in example 1. The pressure is raised to 13,000 kPa of the same gas mixture and the temperature is raised to 70° C. After 2 h 30, the gas absorption amounts to 0.26 mole.

After cooling, the content of the reactor is analysed and shows the formation of 0.063 mole of N-acetyliminodiacetic acid corresponding to a 42% yield with respect to the initial acetamide.

What is claimed is:

1. A process for manufacturing a N-acyliminodiacetic acid by reacting formaldehyde or at least one formaldehyde generator with at least one amide unsubstituted on the nitrogen atom or with at least one generator of an amide unsubstituted on the nitrogen atom and with carbon monoxide, in the presence of a carbonylation catalyst, characterized in that the reaction is performed with a ratio of at least 2:1 of the aldehyde groups or generators thereof to the amide groups or generators thereof.

2. A process according to claim 1, wherein the amide is of the general formula $RCONH_2$ wherein R is hydrogen or an aliphatic, cycloaliphatic, aromatic or heterocyclic radical.

3. A process according to claim 1, wherein the amide is obtained in situ by hydrolyzing a nitrile or reacting ammonia with a carboxylic ester, acid or anhydride.

4. A process according to claim 1, wherein formaldehyde is present in the pure form, in a polymeric form or as derivative thereof.

5. A process according to claim 1, wherein formaldehyde or its derivatives and the amide or the generators thereof are supplied in a molar proportion of 2:1 3:1.

6. A process according to claim 1, wherein the catalyst is a cobalt compound.

7. A process according to claim 1, wherein the carbon monoxide pressure is from 5,000 to 30,000 kPa.

8. A process according to claim 1, wherein the reaction temperature is from 50° to 150° C.

* * * * *